(12) United States Patent
Ahn

(10) Patent No.: US 8,771,225 B2
(45) Date of Patent: Jul. 8, 2014

(54) BALLOON CATHETER

(75) Inventor: Yong Chul Ahn, Seongnam-si (KR)

(73) Assignee: Yong Chul Ahn, Seongnam-si (KR)

( * ) Notice: Subject to any disclaimer, the term of this patent is extended or adjusted under 35 U.S.C. 154(b) by 0 days.

(21) Appl. No.: 13/814,605

(22) PCT Filed: Sep. 14, 2010

(86) PCT No.: PCT/KR2010/006245
§ 371 (c)(1),
(2), (4) Date: Feb. 6, 2013

(87) PCT Pub. No.: WO2012/020883
PCT Pub. Date: Feb. 16, 2012

(65) Prior Publication Data
US 2013/0138039 A1 May 30, 2013

(30) Foreign Application Priority Data
Aug. 12, 2010 (KR) .......................... 10-2010-0077882

(51) Int. Cl.
*A61M 29/00* (2006.01)
*A61M 25/10* (2013.01)
*A61M 25/00* (2006.01)

(52) U.S. Cl.
CPC .......... *A61M 25/1025* (2013.01); *A61M 25/007* (2013.01); *A61M 25/10* (2013.01)
USPC ............... 604/102.01; 604/96.01; 604/102.03

(58) Field of Classification Search
CPC ............ A61M 25/10; A61M 25/0108; A61M 25/007; A61M 25/1025
USPC .......................................... 604/96.01–103.06
See application file for complete search history.

(56) References Cited

U.S. PATENT DOCUMENTS

| | | | | |
|---|---|---|---|---|
| 5,458,573 A | * | 10/1995 | Summers | 604/101.04 |
| 2002/0010420 A1 | * | 1/2002 | Bagaoisan et al. | 604/103.11 |
| 2003/0036804 A1 | * | 2/2003 | Thomas et al. | 623/23.72 |
| 2003/0040736 A1 | * | 2/2003 | Stevens et al. | 604/532 |
| 2003/0220664 A1 | | 11/2003 | Petrick et al. | |
| 2004/0006341 A1 | * | 1/2004 | Shaolian et al. | 606/61 |
| 2005/0015048 A1 | * | 1/2005 | Chiu et al. | 604/101.04 |
| 2005/0267409 A1 | * | 12/2005 | Shkolnik | 604/103.06 |
| 2008/0082046 A1 | * | 4/2008 | Kato et al. | 604/101.01 |
| 2008/0147001 A1 | * | 6/2008 | Al-Marashi et al. | 604/103.04 |
| 2009/0018498 A1 | * | 1/2009 | Chiu et al. | 604/97.02 |
| 2009/0312806 A1 | * | 12/2009 | Sherman et al. | 606/86 R |

FOREIGN PATENT DOCUMENTS

| | | |
|---|---|---|
| JP | S57-191178 U | 6/1984 |
| JP | 531194 A | 2/1993 |
| JP | 8-308933 A | 11/1996 |
| JP | 200137882 A | 2/2001 |
| JP | 2002-095753 A | 4/2002 |
| JP | 2004147737 A | 5/2004 |
| JP | 2005-518903 A | 6/2005 |
| JP | 2006-334222 A | 12/2006 |
| KR | 1020090040624 A | 4/2009 |
| WO | 03/075976 A2 | 9/2003 |

* cited by examiner

*Primary Examiner* — Nicholas Lucchesi
*Assistant Examiner* — Gerald Landry, II
(74) *Attorney, Agent, or Firm* — The Webb Law Firm

(57) ABSTRACT

A balloon catheter is configured so that a balloon can be easily inserted into the interior of a human body without using a separate wire.

19 Claims, 14 Drawing Sheets

BALLOON CATHETER

BACKGROUND OF THE INVENTION

1. Field of the Invention

The present invention relates to a medical balloon catheter.

2. Description of the Related Art

Generally, medical balloon catheters include a tube extending in a lengthwise direction, a balloon bonded to one of opposite ends of the tube that undergoes expansion and contraction in response to the adjustment of internal pressure, and a connector fixed to the other end of the tube and connected with, for instance, a syringe injecting a substance via the tube.

Such balloon catheters are designed so that the balloon is inserted into an internal blood vessel, internal tissue, or a bone lumen in a contracted state, and then is expanded. Thus, the internal blood vessel, the internal tissue, or the bone lumen is dilated.

Meanwhile, the tube is provided therein with two passages extending in a lengthwise direction thereof. A guide wire is inserted into one of these two passages. The guide wire serves not only to reinforce stiffness of the tube and prevent the tube from being arbitrarily bent when the tube is inserted into the human body, but also allows the tube to be guided into the human body. The other of the two passages communicates with the interior of the balloon and is configured so that a fluid pressurizing the interior of the balloon flows therethrough.

Since the tube of this balloon catheter must be separately provided with the passage into which the guide wire is inserted and the passage through which a substance for dilating the balloon flows, it is not easy to manufacture the balloon catheter.

Further, since an insertion port into which the guide wire is inserted and an injection port into which a material for expanding the balloon is injected must be separately formed in the connector connected to the other end of the tube, the connector has a complicated structure. Further, the diameter of the tube is increased, and thus a patient experiences pain when the tube is inserted into the interior of the body. In a process of manufacturing the balloon catheter, a process of connecting the insertion and injection ports of the connector with the two passages of the tube respectively is complicated.

In particular, this balloon catheter must insert the guide wire having higher stiffness than the tube into the passage of the tube in order to enable a surgeon to insert the tube formed of flexible material into the interior of the body, so that the surgeon must separately deal with the tube and the guide wire.

SUMMARY OF THE INVENTION

Accordingly, the present invention has been made keeping in mind the above problems occurring in the related art, and embodiments of the present invention provide a balloon catheter capable of reducing the inconvenience of a surgeon because the balloon catheter has a simple construction.

According to one aspect of the present invention, there is provided a balloon catheter, which includes: a first sub-tube, which extends in the lengthwise direction, has a first end and a second end, and has a first passage formed therein; a second sub-tube, which has a first end attached to an outer circumference of the first sub-tube and located at the same position as the first end of the first sub-tube, an extension section extending beyond the second end of the first sub-tube and having a second passage formed therein and a through-hole formed in an outer circumference thereof, and a second end having an opening communicating with the extension section, the second passage communicating with the first end of the first sub-tube; and a balloon disposed on the extension section of the second sub-tube.

Here, the extension section of the second sub-tube may have a first identification mark attached thereto. The first identification mark may be formed of platinum, iridium, or an alloy thereof that can be clearly identified by radiation imaging equipment such as X-ray equipment or C-ARM.

Meanwhile, to maintain a shape of the second end of the second sub-tube so that it is not deformed, a seal member may be is inserted into the opening of the extension section of the second sub-tube to seal the opening. Here, the seal member may have a second identification mark attached to a part thereof. Further, the seal member may extend into the extension section of the second sub-tube.

The first sub-tube may be formed of a metal having higher stiffness than the second sub-tube so as to be able to reinforce the stiffness of the tube such that the tube is not greatly bent when the balloon is inserted into the interior of a human body. Here, the first sub-tube may be formed of a shape memory alloy, such as a nitinol alloy, which is a non-magnetic alloy of titan and nickel, such that the tube can maintain its original state after force applied to the tube is released.

The second sub-tube may be formed of a synthetic resin, so that it can closely cover the outer circumference of the first sub-tube formed of a metal and the balloon can be fused to the outer circumference of the second sub-tube.

Meanwhile, the balloon catheter may further include a third sub-tube, which is connected with the second end of the first sub-tube, is disposed inside the second passage of the second sub-tube, and is formed so as to be able to extend in a lengthwise direction. Here, the third sub-tube may be formed in a spiral coil shape so as to be able to extend in a lengthwise direction.

Meanwhile, the first sub-tube may be formed in a spiral coil shape, without only the first sub-tube being formed in the spiral coil shape.

The balloon catheter may further include: a protection tube, which is disposed on the outer circumference of the second sub-tube so as to be able to move in the lengthwise direction of the tube and protect the balloon; and a stopper member, which prevents the protection tube from arbitrarily moving in the lengthwise direction of the tube.

Here, the stopper member may include: a first end having an inner diameter substantially identical to an outer diameter of the second sub-tube; a second end having a larger outer diameter than an inner diameter of the protection tube; and a slot cut between the first and second ends in a lengthwise direction of the stopper member.

Further, the protection tube and/or the stopper member may include a grip. Further, the protection tube may have an identification mark attached thereto.

Meanwhile, the first sub-tube may extend into the extension section of the second sub-tube in order to reinforce stiffness of the extension section of the second sub-tube.

According to exemplary embodiments of the present invention, the balloon catheter disposes one sub-tube having stiffness in the other sub-tube, so that it is possible to form only one passage, through which fluid for expanding the balloon flows, in the tube, and to exclude the use of a guide wire applied to a conventional balloon catheter. As a result, it is possible to simplify the process of manufacturing the balloon catheter, and to reduce the inconvenience of a surgeon, compared to the related art.

BRIEF DESCRIPTION OF THE DRAWINGS

The above and other objects, features and advantages of the present invention will be more clearly understood from the following detailed description when taken in conjunction with the accompanying drawings, in which.

DETAILED DESCRIPTION OF THE INVENTION

Figure 1:
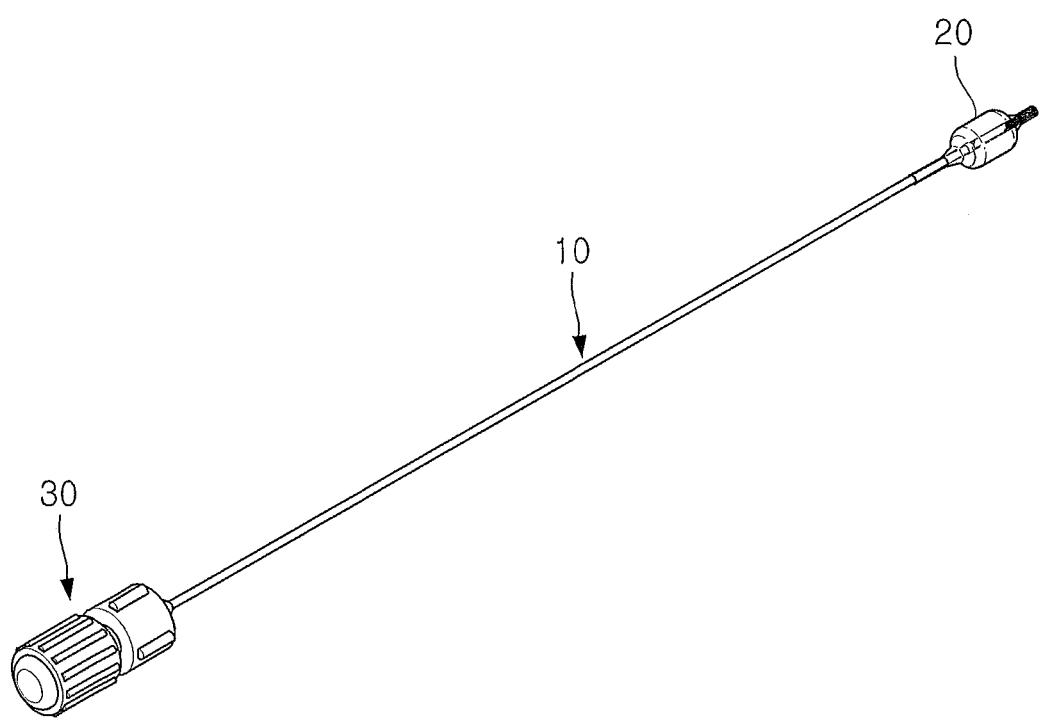
FIG. 1 is a perspective view illustrating a balloon catheter according to a first embodiment of the present invention.
Figure 2:
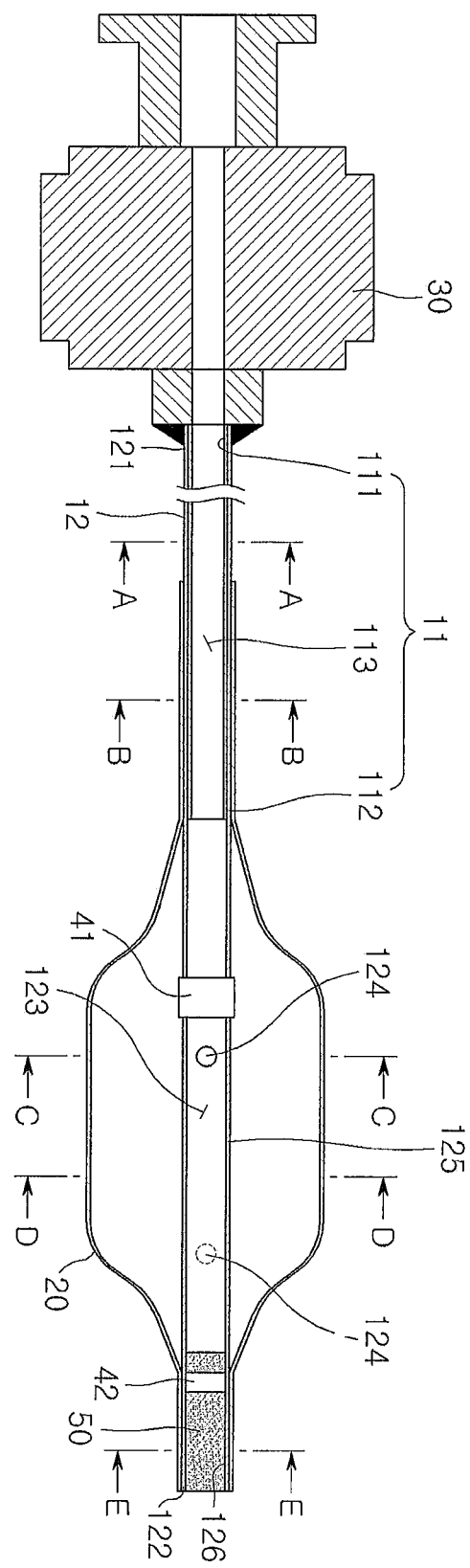
FIG. 2 is a cross-sectional view illustrating key parts of the balloon catheter of FIG. 1.
Figure 3:
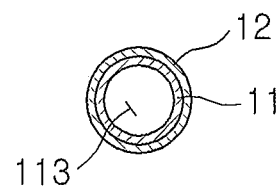
FIG. 3 is a cross-sectional view taken along line A-A of FIG. 2.
Figure 4:
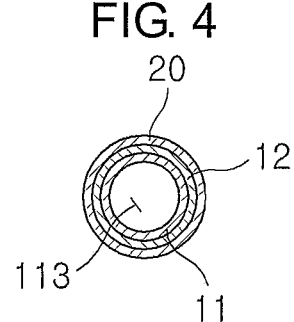
FIG. 4 is a cross-sectional view taken along line B-B of FIG. 2.
Figure 5:
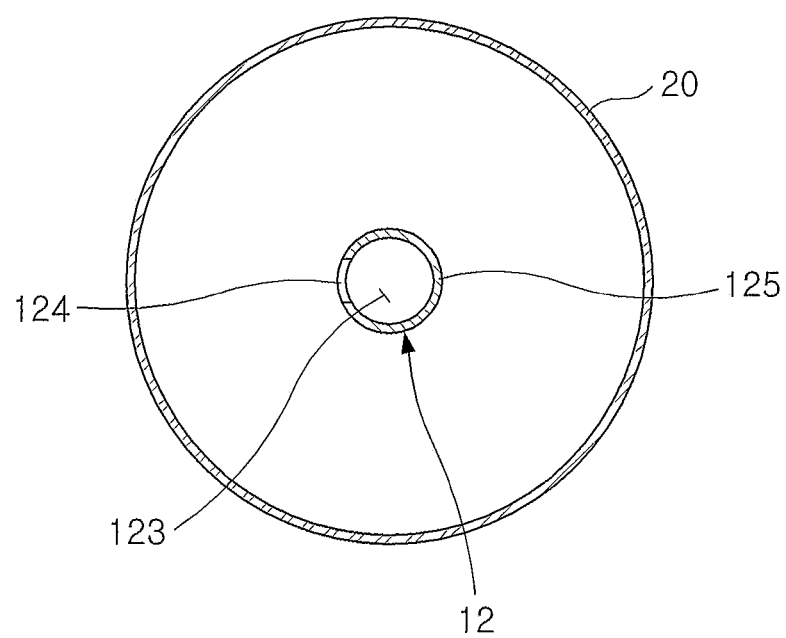
FIG. 5 is a cross-sectional view taken along line C-C of FIG. 2.
Figure 6:
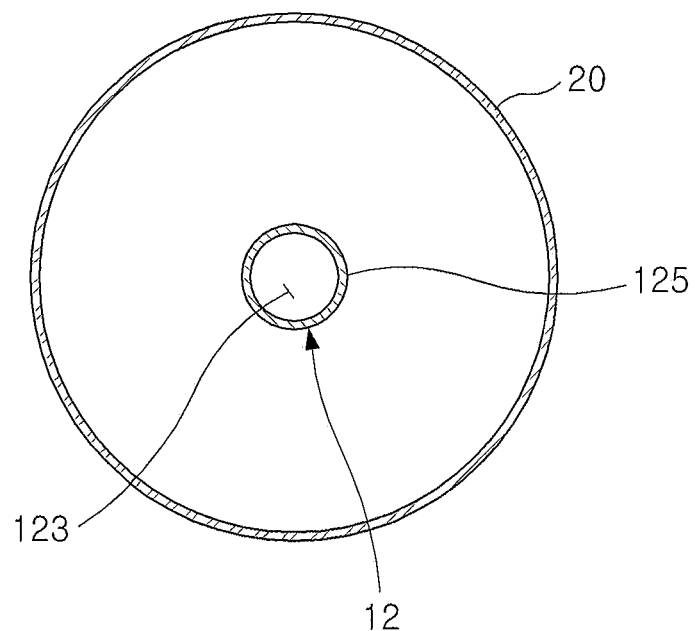
FIG. 6 is a cross-sectional view taken along line D-D of FIG. 2.
Figure 7:
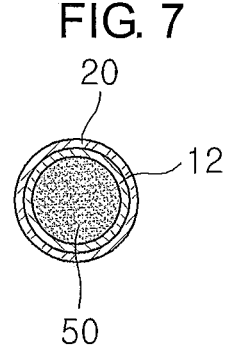
FIG. 7 is a cross-sectional view taken along line E-e of FIG. 2.

Reference will now be made in greater detail to exemplary embodiments of the invention with reference to the accompanying drawings. Wherever possible, the same reference numerals will be used throughout the drawings and the description to refer to the same or like parts.

As illustrated in FIG. 1, a balloon catheter according to a first exemplary embodiment of the present invention includes a tube 10 extending in a lengthwise direction, a balloon 20 fixed to one of opposite ends of the tube 10 and inserted into the interior of the body such as in a blood vessel, a lumen of the bowel, or a lumen of a bone so as to be expanded or contracted in response to the adjustment of internal pressure, and a connector 30 fixed to the other end of the tube 10 and connecting the tube 10 to, for instance, a syringe (not shown) which is for injecting a fluid that expands the balloon 20 into the tube 10.

As illustrated in FIGS. 2 through 7, the tube 10 includes a first hollow sub-tube 11, which extends in the lengthwise direction of the tube 10, has a first end 111 and a second end 112, and is provided therein with a first passage 113, and a second sub-tube 12, which is closely attached to an outer circumference of the first sub-tube 11 in a lengthwise direction of the first sub-tube 11.

The first sub-tube 11 is formed of a metal that is stiffer than is the second sub-tube 12. This first sub-tube 11 serves to reinforce stiffness of the tube 10 such that the tube 10 is not excessively bent when the balloon 20 of the tube 10 is inserted into the human body. The first sub-tube 11 may be formed of stainless steel. Alternatively, the first sub-tube 11 may be formed of a shape memory alloy, such as a nitinol alloy that is a non-magnetic alloy of titan and nickel, such that the tube 10 can maintain its original state after force applied to the tube 10 is released. Of course, the material for the first sub-tube 11 is not limited to the metal. As long as the first sub-tube 11 is stiff enough to reinforce the stiffness of the tube 10, a synthetic resin (polymer) may be used as the material for the first sub-tube 11.

The second sub-tube 12 includes a first end 121 disposed at the same position as the first end 111 of the first sub-tube 11, an extension section 125 that extends beyond the second end 112 of the first sub-tube 11, is provided therein with a second passage 123 communicating with the first passage 113 of the first sub-tube 11, and has at least one through-hole 124 in an outer circumference thereof, and a second end 122 having an opening 125 communicating with the extension section 125.

The balloon 20 is disposed on the extension section 125 of the second sub-tube 12, and its interior communicates with the first passage 113 via the through-hole 124 and the second passage 123. The balloon 20 is formed of a synthetic resin that can be expanded and contracted. The balloon 20 may be bonded to an outer circumference of the second sub-tube 12 under pressure and heat at opposite ends thereof.

The second sub-tube 12 may be closely covered on the outer circumference of the first sub-tube 11 formed of the metal, and be formed of a synthetic resin such that the balloon 20 can be bonded on the outer circumference of the second sub-tube 12. Also, the second sub-tube 12 may be formed of the same material, the synthetic resin (polymer), as the material of the balloon 20.

The extension section 125 of the second sub-tube 12 extends beyond the second end 112 of the first sub-tube 11, and corresponds to a portion that is not covered on the outer circumference of the first sub-tube 11. This extension section 125 can extend in a lengthwise direction when the balloon 20 is expanded.

Meanwhile, when performing an operation using the balloon catheter, a surgeon checks the position of the balloon of the balloon catheter in the interior of the body using radiation imaging equipment such as X-ray equipment or C-ARM. Here, a first identification mark 41 may be attached to the outer circumference of the extension section 125 of the second sub-tube 12 such that the surgeon can more easily check the position of the balloon using the radiation imaging equipment. The first identification mark 41 may be formed of a metal such as platinum, iridium, or an alloy thereof that can be clearly identified by the radiation imaging equipment such as X-ray equipment or C-ARM. Alternatively, the first identification mark 41 may be formed of a synthetic resin (polymer) that is the same material as the balloon 20. The first identification mark 41 may be attached to the outer circumference of the extension section 125 of the second sub-tube 12 in a tape shape.

The second sub-tube 12 may be formed of a flexible material such that the extension section 125 that is not covering the outer circumference of the first sub-tube 11 can extend to a predetermined length when the balloon 20 is expanded.

A seal member 50 for sealing the opening 126 may be inserted into the second end 122 of the second sub-tube 12. A second identification mark 42 formed of the same material as the first identification mark 41 attached to the extension section 125 of the second sub-tube 12 may be attached to a part of the seal member 50 inserted into the opening 126. Meanwhile, the present exemplary embodiment is not limited to the construction where the seal member 50 is inserted into the opening 126 of the second sub-tube 12. For example, the opening 126 may be sealed by thermally fusing an inner circumference of the second end 122 of the second sub-tube 12 by which the opening 126 of the second sub-tube 12 is defined. However, the structure where the seal member 50 is inserted into and sealed in the opening 126 of the second sub-tube 12 is easier to manufacture, compared to the structure where the portion defining the opening 126, i.e. the inner circumference of the second end 122, is fused.

The seal member 50 may be formed in the shape of a cylinder having an outer diameter corresponding to an inner diameter of the opening 126 of the second sub-tube 12. The seal member 50 may be inserted into the opening 126 in close contact with the opening 126. To prevent the seal member 50 from accidentally separating from the opening 126, the opening 126 of the second sub-tube 12 is heated to fuse the second sub-tube 12 to an outer surface of the seal member 50, so that the seal member 50 can be coupled with the second sub-tube 12. The seal member 50 is formed of a material having a relatively high stiffness, and is inserted into the opening 126 to so that a leading end of the tube 10, i.e. the second end 122 of the second sub-tube 12, can maintain its shape, without being deformed. Thus, while the balloon 20 is being inserted into the interior of the body, the leading end of the tube 10 can be prevented from deforming.

The first end 111 of the first sub-tube 11 and the first end 121 of the second sub-tube 12 may be connected to one end of the connector 30. The connector 30 and the first sub-tube 11 and the second sub-tube 12 may be connected by, for instance, an adhesive, or a separate fastener. The other end of the connector 30 may be connected with, for instance, a syringe that injects liquid that expands the balloon 20.

With this construction, the balloon 20 is inserted into the interior of the body past a pre-bored hole in a contracted state. Here, the tube 10 is reinforced in stiffness by the first sub-tube 11, so that it is possible to prevent the tube 10 from being bent without using a separate guide wire.

Meanwhile, the fluid that expands the balloon 20 is injected into the first passage 113 of the first sub-tube 11 by, for instance, the syringe connected to the connector 30 in the state where the balloon 20 has been inserted into the interior of the body. Here, since the tube 10 is reinforced in stiffness by the first sub-tube 11, the tube 10 is prevented from being deformed by pressure of the fluid while the fluid flows through the first passage 113 of the first sub-tube 11.

The fluid injected into the first passage 113 flows into an internal space of the balloon 20 via the second passage 123 and the through-hole 124, so that the pressure of the fluid introduced into the internal space of the balloon 20 expands the balloon 20.

Thus, a region to be operated on such as an internal blood vessel, a lumen of the bowel, or a lumen of the bone is expanded by the expanding balloon 20, and thus the relevant operation can be performed. After the operation is completed, the fluid inside the balloon 20 is discharged to the outside via the through-hole 124, the second passage 123, and the first passage 113, and thus the balloon 20 is contracted into the state before it is expanded, so that the balloon 20 can be removed from the interior of the body.

The balloon catheter according to the first exemplary embodiment of the present invention is manufactured by preparing the first hollow sub-tube 11 having higher stiffness than the second sub-tube 12, covering the outer circumference of the first sub-tube 11 which is shorter than the second sub-tube 12 so that this difference in length forms the extension section 125 of the second sub-tube 12, attaching the identification mark 41 to the extension section 125 of the second sub-tube 12, fusing the opposite ends of the balloon 20 to the second sub-tube 12 such that the balloon 20 is disposed at the extension section 125 of the second sub-tube 12, and inserting the seal member 50 into the opening 126 of the second sub-tube 12. This method of manufacturing the balloon catheter according to the first exemplary embodiment of the present invention is simpler than a method of manufacturing a conventional balloon catheter in which two passages must be formed in the tube 10.

In the balloon catheter, as described above, according to the first exemplary embodiment of the present invention, since the stiffness of the tube 10 is reinforced by the first hollow sub-tube 11 that is stiffer than the second sub-tube 12, it is possible to prevent the tube 10 from being greatly bent when the balloon 20 is inserted into the interior of the body, and to easily insert the balloon 20 into the interior of the body without using a separate guide wide as in the conventional balloon catheter. Thus, the balloon catheter according to the first exemplary embodiment of the present invention can eliminate the inconvenience of the surgeon compared to the conventional balloon catheter in which the surgeon must deal with the tube as well as the guide wire.

Further, in the balloon catheter according to the first exemplary embodiment of the present invention, since it is sufficient for only one injection port, into which the fluid for expanding the balloon 20 is injected, to be formed in the connector 30 connected with the tube 10, the process of manufacturing the connector 30 and the process of connecting the connector 30 to the tube 10 can be simplified.

Hereinafter, a balloon catheter according to a second exemplary embodiment of the present invention will be described with reference to FIGS. 8 through 10. The part(s) identical to the part(s) described in the first exemplary embodiment of the present invention will be given the same reference numeral (s), and thus a detailed description thereof will be omitted.

Figure 8:
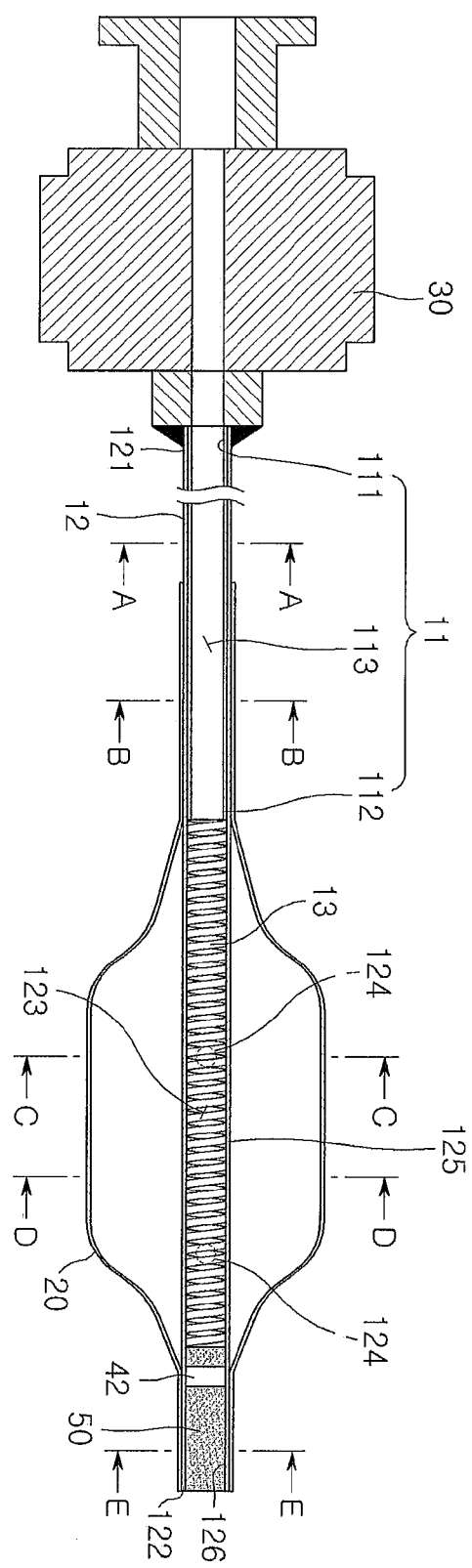
FIG. 8 is a cross-sectional view illustrating key parts of a balloon catheter according to a second embodiment of the present invention.
Figure 9:
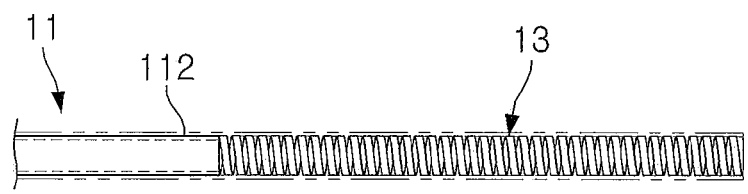
FIG. 9 is a side view illustrating first and third sub-tubes of the balloon catheter of FIG. 8.
Figure 10:
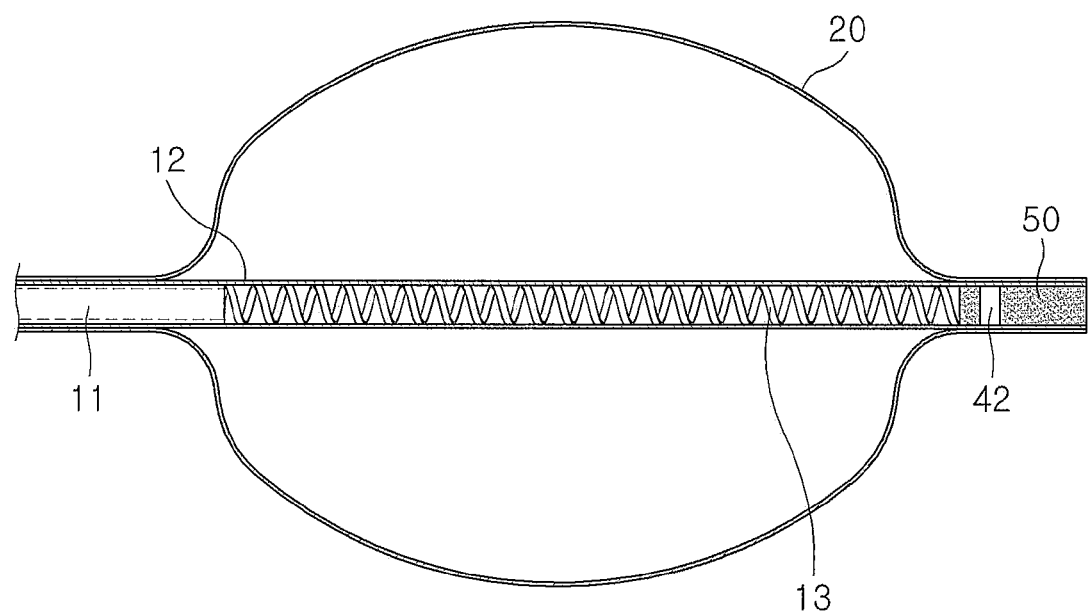
FIG. 10 is a side view illustrating the state where a third sub-tube of the balloon catheter of FIG. 8 extends in a lengthwise direction.

As illustrated in FIGS. 8 through 10, the balloon catheter according to the second exemplary embodiment of the present invention may further include a third sub-tube 13, which is connected with the second end 112 of the first sub-tube 11, is disposed in the second passage 123 of the second tub-tube 12, and is formed so as to be able to extend in a lengthwise direction.

The third sub-tube 13 may be formed in a spiral coil shape such that it can extend in a lengthwise direction.

Meanwhile, the extension section 125 of the second sub-tube 12 may be covered on an outer surface of the third sub-tube 13 by, for instance, fusion. Thereby, as illustrated in FIG. 10, when the balloon 20 is expanded, the extension section 125 of the second sub-tube 12 extends in a lengthwise direction, so that the third sub-tube 13 can extend in a lengthwise direction.

The third sub-tube 13 may be formed of a metal or shape memory alloy, which is the same material as the first sub-tube 11.

The third sub-tube 13 may be connected to the second end 112 of the first sub-tube 11 by welding, fusion, or the like. The second exemplary embodiment of the present invention is not limited to this method of connection. For example, the third sub-tube 13 may be integrally formed with the first sub-tube 11. When the third sub-tube 13 is integrally formed with the first sub-tube 11, the first sub-tube 11 may be formed in the same shape as the third sub-tube 13 by the process of cutting one end of a metal tube and its neighboring portion in a spiral line.

With this construction, when the tube 10 and the balloon 20 are inserted into the interior of the body, the first sub-tube 11 and the third sub-tube 13 can reinforce the stiffness of the tube 10, so that the leading end of the tube 10, i.e. the portion corresponding to the extension section 125 of the second sub-tube 12, can be prevented from bending a lot when the balloon 20 is inserted into the interior of the body.

Further, when the third sub-tube 13 is formed of a metal, and particularly a metal such as platinum, iridium, or an alloy thereof that can be clearly identified by radiation imaging equipment such as X-ray equipment or C-ARM, a surgeon can easily determine the position of the balloon 20 using the radiation imaging equipment even when a separate identification mark is not attached to the second sub-tube 12. Thus, when the third sub-tube 13 is formed of a metal, it is possible to exclude the attachment of the identification mark, so that the process of attaching the identification mark can be removed, and thus the cost required to attach the identification mark can be eliminated.

In this way, the third sub-tube 13 serves to prevent the leading end of the tube 10 from bending when the balloon 20 is inserted into the interior of the body, and to extend in a lengthwise direction such that the balloon 20 can expand. Meanwhile, when the balloon 20 is contracted, the third sub-tube 13 can be contracted in a lengthwise direction by its own resilient restoring force.

Meanwhile, the second exemplary embodiment of the present invention is not limited to the construction where only the third sub-tube 13 is formed in the spiral coil shape. Alternatively, the first sub-tube 11 may also be formed in a spiral coil shape. In this case, the first sub-tube 11 can be bent to some extent. Thus, since the first sub-tube 11 not only reinforces the stiffness of the tube 10 when the balloon 20 is inserted but also is bent to some extent, it is possible to easily adjust the angle at which the balloon 20 is inserted, and the tube 10 can be bent at a predetermined angle in the state where the balloon 20 has been inserted into the interior of the body.

Hereinafter, a balloon catheter according to a third exemplary embodiment of the present invention will be described with reference to FIGS. 11 through 13. The part(s) identical to the part(s) described in the first and second exemplary embodiments of the present invention will be given the same reference numeral(s), and thus a detailed description thereof will be omitted.

Figure 11:
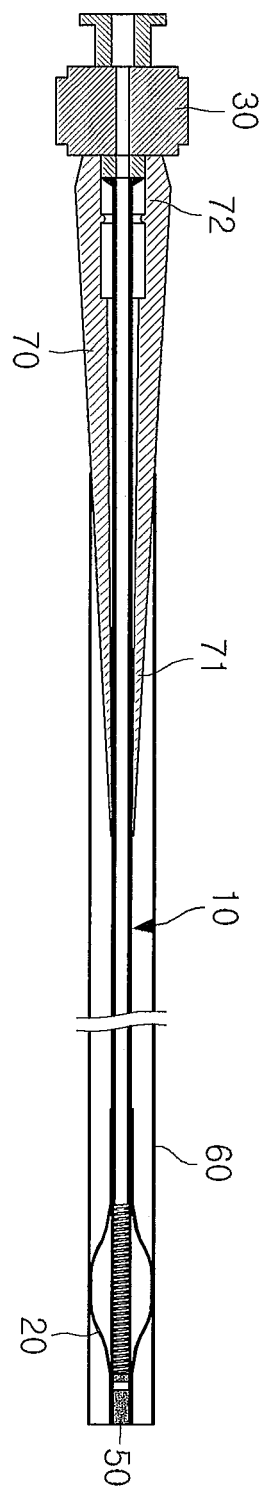
FIG. 11 is a cross-sectional view illustrating a balloon catheter according to a third embodiment of the present invention.
Figure 12:
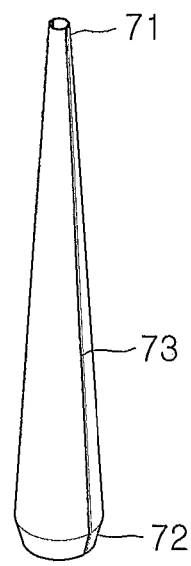
FIG. 12 is a perspective view illustrating a stopper member of the balloon catheter of FIG. 11.
Figure 13:
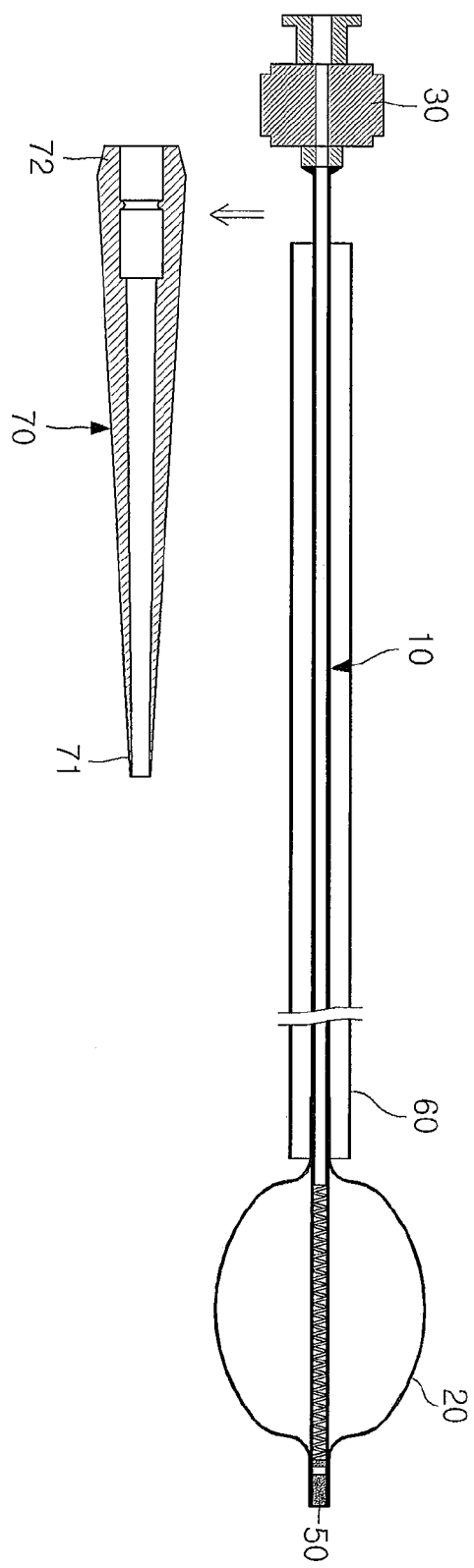
FIG. 13 is a side view illustrating the state wherein the protection of the balloon of the balloon catheter of FIG. 11 has been released.

As illustrated in FIGS. 11 through 13, the balloon catheter according to the third exemplary embodiment of the present invention may include a protection tube 60 disposed on an outer circumference of the tube 10 so as to be able to move in a lengthwise direction of the tube 10 and protecting the balloon 20, and a stopper member 70 that prevents the protection tube 60 from arbitrarily moving in the lengthwise direction of the tube 10.

The inner diameter of the protection tube 60 is such that the balloon 20 can be inserted along with the tube 10 in the state where the balloon 20 is contracted.

As illustrated in FIG. 12, the stopper member 70 is formed of a resilient material in a hollow shape. The stopper member 70 includes a first end 71 having an inner diameter substantially identical to an outer diameter of the tube 10, i.e. an outer diameter of the second sub-tube 12, a second end 72 having a larger outer diameter than the inner diameter of the protection tube 60, and a slot 73 cut between the first and second ends 71 and 72 in a lengthwise direction of the stopper member 70. The stopper member 70 may be formed to have its outer diameter gradually increase from the first end 71 to the second end 72.

The tube 10 may be fitted into the stopper member 70 through the slot 73 of the stopper member 70. Here, the first end 71 of the stopper member 70 is directed toward the balloon 20, and the second end of the stopper member 70 may be in close contact with the connector 30.

With this construction, as illustrated in FIG. 11, the protection tube 60 is kept from moving in the lengthwise direction of the tube 10 by the stopper member 70 after being fitted into the first end 71 of the stopper member 70. Here, the protection tube 60 is located so as to surround the balloon 20, and thus the balloon 20 is prevented from being damaged, for instance scratched, when it makes contact with another external device or tool.

Meanwhile, after the balloon 20 has been inserted into the interior of the body in the state wherein it is protected by the protection tube 60, the balloon 20 may be expanded in the interior of the body in the state where the protection by the protection tube 60 is released. Of course, if necessary, the balloon 20 may be inserted into the interior of the body in the state where the protection by the protection tube 60 is released.

As illustrated in FIG. 13, the protection of the balloon 20 by the protection tube 60 may be released by removing the stopper member 70 from the tube 10 via the slot 73 and pulling the protection tube 60 toward the connector 30.

The balloon catheter, as described above, according to the third exemplary embodiment of the present invention, includes the protection tube 60 and the stopper member 70 preventing the arbitrary movement of the protection tube 60, so that it is possible to prevent the balloon 20 from being damaged by an external device or tool before the balloon 20 is expanded.

Hereinafter, a balloon catheter according to a fourth exemplary embodiment of the present invention will be described with reference to FIGS. 14 through 16. The part(s) identical to the part(s) described in the first to third exemplary embodiments of the present invention will be given the same reference numeral(s), and thus a detailed description thereof will be omitted.

Figure 14:
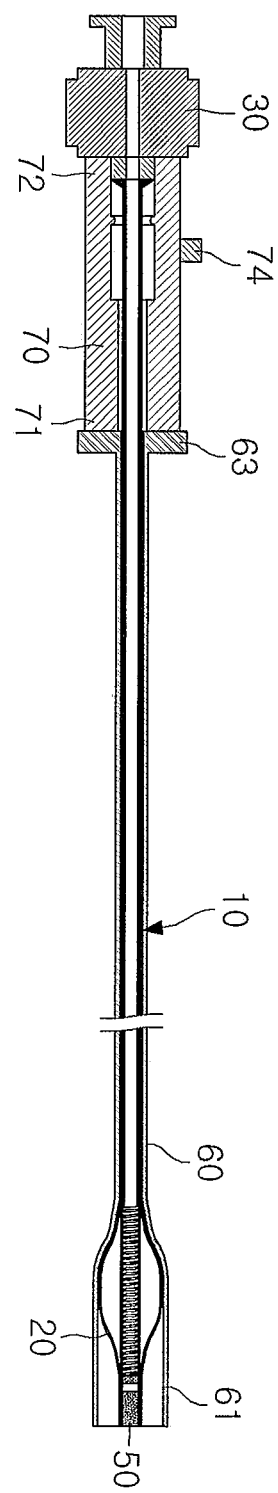
FIG. 14 is a cross-sectional view illustrating a balloon catheter according to a fourth embodiment of the present invention.
Figure 15:
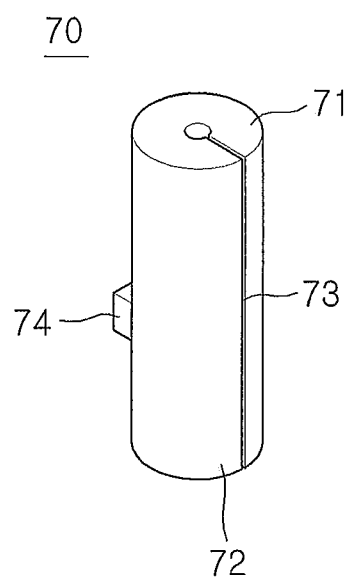
FIG. 15 is a perspective view illustrating a stopper member of the balloon catheter of FIG. 14.
Figure 16:
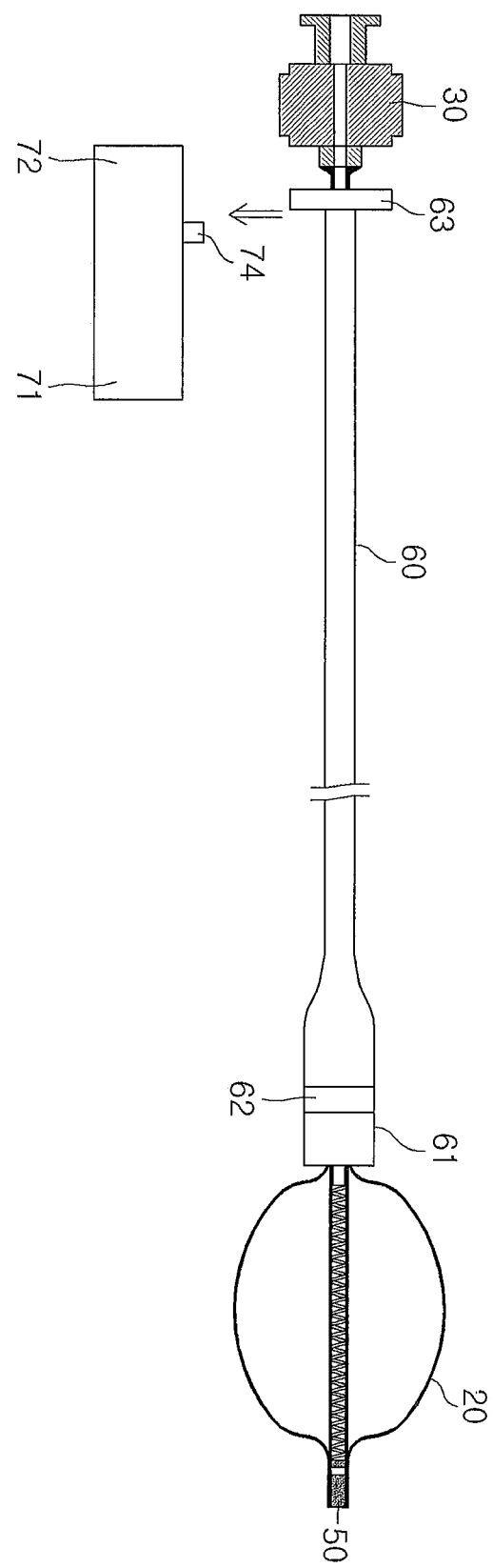
FIG. 16 is a side view illustrating the state wherein protection of the balloon of the balloon catheter of FIG. 14 has been released.

As illustrated in FIGS. 14 through 16, the balloon catheter according to the fourth exemplary embodiment of the present invention may include a protection tube 60 disposed on an outer circumference of the tube 10 so as to be able to move in a lengthwise direction of the tube 10 and protect the balloon 20, and a stopper member 70 preventing the protection tube 60 from arbitrarily moving in the lengthwise direction of the tube 10.

As illustrated in FIG. 15, the stopper member 70 has a hollow shape, and includes a first end 71 having an inner diameter substantially identical to an outer diameter of the tube 10, i.e. an outer diameter of the second sub-tube 12, a second end 72 having a larger outer diameter than the inner diameter of the protection tube 60, and a slot 73 cut between the first and second ends 71 and 72 in a lengthwise direction of the stopper member 70.

The tube 10 may be fitted into the stopper member 70 through the slot 73 of the stopper member 70. A grip 74 may protrude from the stopper member 70 such that a surgeon can easily remove the stopper member 70 from the tube 10.

The protection tube 60 is formed in a hollow shape and its inner diameter is substantially the same as the outer diameter of the tube 10. The tube 60 has an extension section 61, a diameter of which is increased so as to correspond to the outer diameter of the balloon 20, at a portion where it covers the balloon 20. In other words, the inner diameter of the protection tube 60 corresponds to the outer diameters of the tube 10 and the balloon 20. With this construction, the protection tube 60 can make close contact with the outer circumferences of the tube and the balloon 20, so that it is possible to prevent the protection tube 60 from arbitrarily moving relative to the tube 10 and the balloon 20.

After the balloon 20 has been inserted into the interior of the body in the state wherein it is protected by the protection tube 60, the balloon 20 may be expanded in the interior of the body in the state after the protection furnished by the protection tube 60 has been released. Of course, if necessary, the balloon 20 may be inserted into the interior of the body in the state where the protection by the protection tube 60 is released.

When the balloon 20 is inserted into the interior of the body in the state where the protection by the protection tube 60 is released, an identification mark 62 may be attached to the protection tube 60 such that a surgeon can easily identify a position of the balloon 20 in the interior of the body using radiation imaging equipment such as X-ray equipment or C-ARM. As illustrated in FIG. 16, the identification mark 62 may be attached to an outer circumference of the extension section 61 of the protection tube 60. The identification mark 62 may be formed of the same material as the above-mentioned identification marks 41 and 42.

As illustrated in FIG. 16, the balloon 20 may stop being protected by the protection tube 60 by removing the stopper member 70 from the tube 10 via the slot 73 and pulling the protection tube 60 toward the connector 30. A grip 74 may be formed on the protection tube 60 so that the protection tube 60 can be easily pulled.

Hereinafter, a balloon catheter according to a fifth exemplary embodiment of the present invention will be described with reference to FIGS. 17 and 18. The part(s) identical to the part(s) described in the first to fourth exemplary embodiments of the present invention are denoted by the same reference numeral(s), and thus a detailed description thereof will be omitted.

Figure 17:
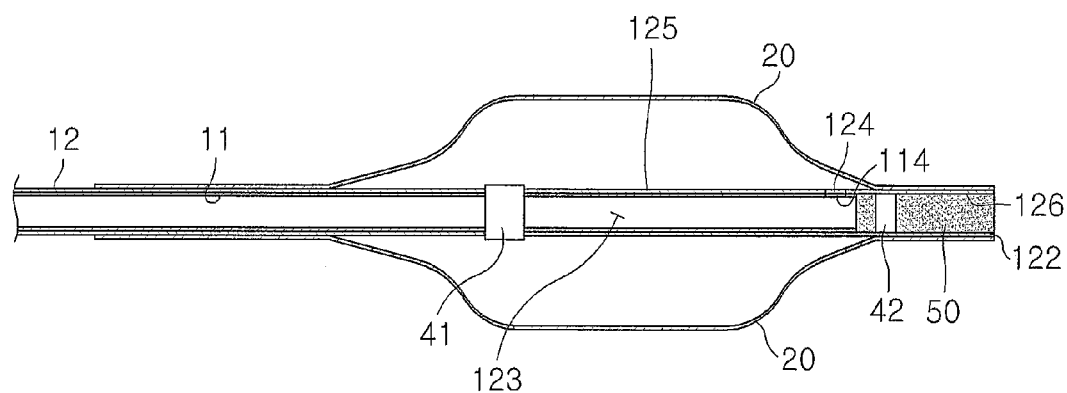
FIG. 17 is a cross-sectional view illustrating a balloon catheter according to a fifth embodiment of the present invention.
Figure 18:
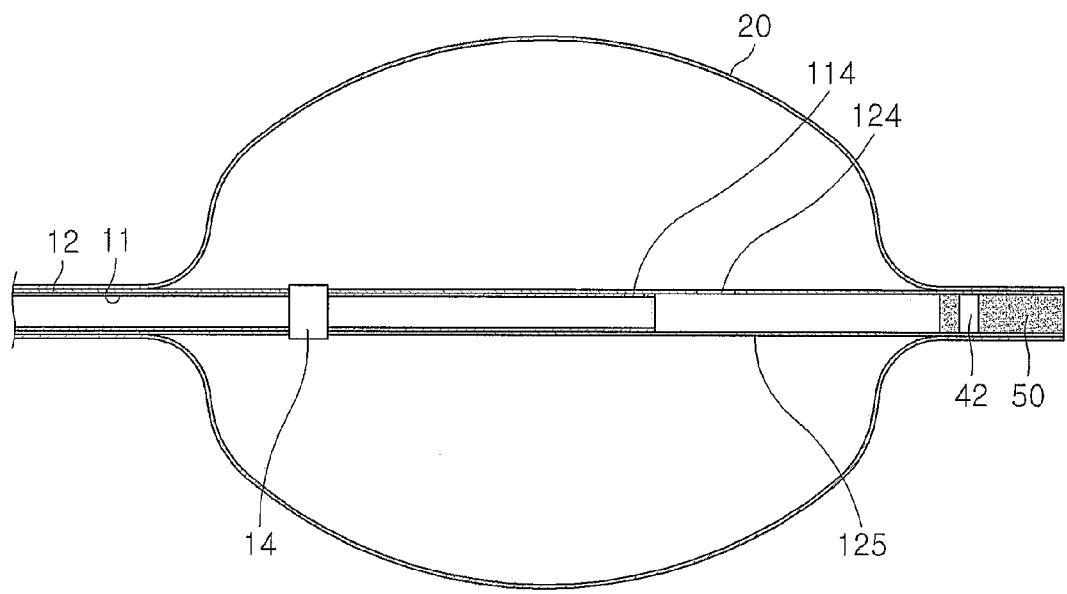
FIG. 18 is a cross-sectional view illustrating the state wherein the balloon of the balloon catheter of FIG. 17 has expanded.

As illustrated in FIG. 17, the balloon catheter according to the fifth exemplary embodiment of the present invention is configured so that the first sub-tube 11 can extend into the extension section 125 of the second sub-tube 12 in the state where the balloon 20 is contracted. The first sub-tube 11 may be provided with a through-hole 114 communicating with the through-hole 124 of the second sub-tube 12.

The extension section 125 of the second sub-tube 12 is not coupled to the first sub-tube 11 at a portion where the first sub-tube 11 is in contact with the extension section 125 of the second sub-tube 12. Thus, as illustrated in FIG. 18, the extension section 125 of the second sub-tube 12 may extend independently of the first sub-tube 11 in a lengthwise direction. With this construction, when the balloon 20 is inserted into the interior of the body, the stiffness of the second sub-tube 12 is reinforced by the first sub-tube 11 over its entirety including the extension section 125, and thus it is possible to prevent the second sub-tube 12 from bending a lot.

Hereinafter, a balloon catheter according to a sixth exemplary embodiment of the present invention will be described with reference to FIGS. 19 and 20. The part(s) identical to the part(s) described in the first to fifth exemplary embodiments of the present invention are denoted by the same reference numeral(s), and thus a detailed description thereof will be omitted.

Figure 19:
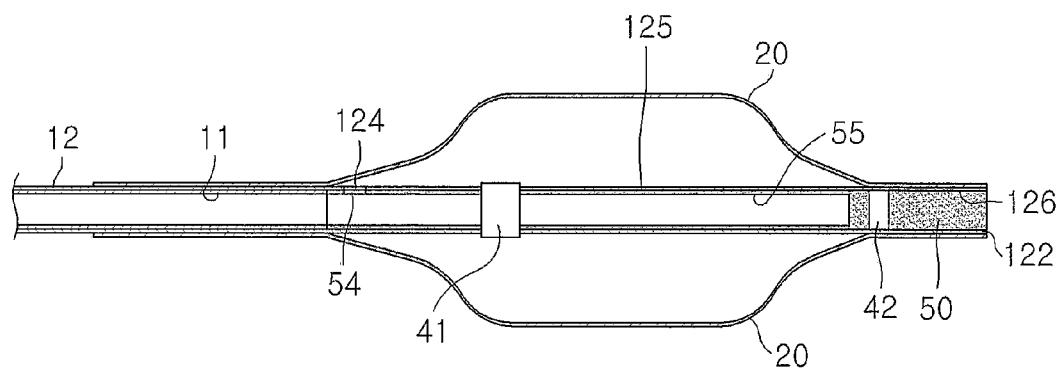
FIG. 19 is a cross-sectional view illustrating a balloon catheter according to a sixth embodiment of the present invention.
Figure 20:
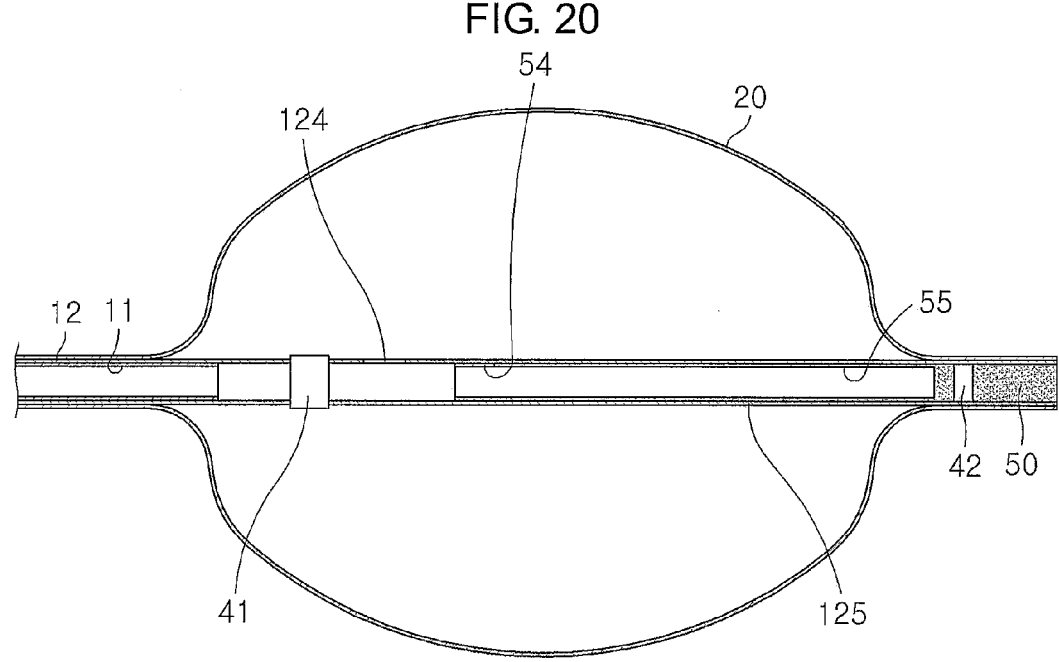
FIG. 20 is a cross-sectional view illustrating the state wherein the balloon of the balloon catheter of FIG. 19 has expanded.

As illustrated in FIG. 19, the balloon catheter according to the sixth exemplary embodiment of the present invention is configured so that a seal member 50 can be extended into the extension section 125 of the second sub-tube 12 in the state where the balloon 20 is contracted. The seal member 50 may be provided with a through-hole 54 communicating with the first passage 113 of the first sub-tube 11 and the through-hole 124 of the second sub-tube 12.

The extension section 125 of the second sub-tube 12 is not coupled to the seal member 50 at a portion where the seal member 50 is contacted with the extension section 125 of the second sub-tube 12. Thus, as illustrated in FIG. 20, the extension section 125 of the second sub-tube 12 may extend independently of the seal member 50 in a lengthwise direction. With this construction, when the balloon 20 is inserted into the interior of the body, the second sub-tube 12 is reinforced in stiffness by the seal member 50, and thus it is possible to prevent the second sub-tube 12 from being greatly bent.

Although exemplary embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A balloon catheter comprising:
   a first sub-tube, which extends in the lengthwise direction, has a first end and a second end, and has a first passage formed therein in order for a fluid to be injected therethrough;
   a second sub-tube, which is attached to an outer circumference of the first sub-tube and has a first end located at a same position as the first end of the first sub-tube, an extension section extending beyond the second end of the first sub-tube and having a second passage formed therein and a through-hole formed in an outer circumference thereof, and a second end having an opening communicating with the extension section, the second passage communicating with the first end of the first sub-tube in order for the fluid to be introduced from the first passage; and
   a balloon disposed on the extension section of the second sub-tube in order for the fluid to be introduced from the through-hole.

2. The balloon catheter as set forth in claim 1, wherein the extension section of the second sub-tube has a first identification mark attached thereto.

3. The balloon catheter as set forth in claim 2, wherein the first identification mark is formed of platinum, iridium, or an alloy thereof.

4. The balloon catheter as set forth in claim 1, further comprising a seal member, which is inserted into the opening of the extension section of the second sub-tube and seals the opening.

5. The balloon catheter as set forth in claim 4, wherein the seal member has a second identification mark attached thereto.

6. The balloon catheter as set forth in claim 5, wherein the seal member extends into the extension section of the second sub-tube.

7. The balloon catheter as set forth in claim 1, wherein the first sub-tube is formed of a metal.

8. The balloon catheter as set forth in claim 1, wherein the first sub-tube is formed of a shape memory alloy.

9. The balloon catheter as set forth in claim 1, wherein the second sub-tube is formed of a synthetic resin.

10. The balloon catheter as set forth in claim 1, further comprising a third sub-tube, which is connected with the second end of the first sub-tube, is disposed inside the second passage of the second sub-tube, and is formed so as to be able to extend in a lengthwise direction.

11. The balloon catheter as set forth in claim 10, wherein the third sub-tube is formed in a spiral coil shape.

12. The balloon catheter as set forth in claim 10, wherein the third sub-tube is formed of a metal.

13. The balloon catheter as set forth in claim 1, wherein the first sub-tube is formed in a spiral coil shape.

14. The balloon catheter as set forth in claim 1, further comprising:

a protection tube, which is disposed on the outer circumference of the second sub-tube so as to be able to move in the lengthwise direction of the tube and protect the balloon; and a stopper member, which prevents the protection tube from arbitrarily moving in the lengthwise direction of the tube.

15. The balloon catheter as set forth in claim 14, wherein the stopper member includes:

a first end having an inner diameter substantially identical to an outer diameter of the second sub-tube;

a second end having a larger outer diameter than an inner diameter of the protection tube; and a slot cut between the first and second ends in a lengthwise direction of the stopper member.

16. The balloon catheter as set forth in claim 14, wherein the protection tube includes a grip.

17. The balloon catheter as set forth in claim 14, wherein the stopper member includes a grip.

18. The balloon catheter as set forth in claim 14, wherein the protection tube has an identification mark attached thereto.

19. The balloon catheter as set forth in claim 1, wherein the first sub-tube extends into the extension section of the second sub-tube.

\* \* \* \* \*